US006764818B2

(12) United States Patent
Lafferty

(10) Patent No.: US 6,764,818 B2
(45) Date of Patent: Jul. 20, 2004

(54) DEVICE FOR EFFECTING HEAT TRANSFER WITH A SOLUTION HELD IN A THROUGH-HOLE WELL OF A HOLDING TRAY

(75) Inventor: William Michael Lafferty, Encinitas, CA (US)

(73) Assignee: Diversa Corporation, San Diego, CA (US)

( * ) Notice: Subject to any disclaimer, the term of this patent is extended or adjusted under 35 U.S.C. 154(b) by 318 days.

(21) Appl. No.: 10/084,026

(22) Filed: Feb. 25, 2002

(65) Prior Publication Data

US 2003/0162307 A1 Aug. 28, 2003

(51) Int. Cl.$^{7}$ .................................................. C12Q 1/00

(52) U.S. Cl. ..................... 435/4; 435/287.2; 435/288.4; 219/674; 219/675; 219/676; 422/102; 422/104; 422/109

(58) Field of Search .......................... 422/99, 101, 102, 422/104, 109; 435/287.2, 4, 288.4; 219/435, 670, 672, 674, 675, 676

(56) References Cited

U.S. PATENT DOCUMENTS

| | | | | | |
|---|---|---|---|---|---|
| D202,700 | S | | 11/1965 | Cooke | |
| 3,634,651 | A | | 1/1972 | Siegel | |
| D246,466 | S | | 11/1977 | Attree | |
| 4,154,795 | A | | 5/1979 | Thorne | |
| 4,256,697 | A | * | 3/1981 | Baldwin | 422/104 |
| 4,299,796 | A | | 11/1981 | Hogen Esch | |
| 4,351,800 | A | * | 9/1982 | Kopp et al. | 422/70 |
| 4,429,829 | A | | 2/1984 | Dutton | |
| D283,162 | S | | 3/1986 | Godsey | |
| 4,599,315 | A | | 7/1986 | Terasaki | |
| 4,735,778 | A | | 4/1988 | Maruyama | |
| 4,824,791 | A | | 4/1989 | Ekholm | |
| 5,061,630 | A | | 10/1991 | Knopf | |
| 5,073,346 | A | | 12/1991 | Partanen | |
| 5,410,130 | A | * | 4/1995 | Braunstein | 219/521 |
| 5,942,432 | A | * | 8/1999 | Smith et al. | 435/303.1 |
| 6,027,873 | A | | 2/2000 | Schellenberger | |
| 6,106,784 | A | * | 8/2000 | Lund et al. | 422/104 |
| 6,140,613 | A | | 10/2000 | Tsuno | |
| 6,210,958 | B1 | * | 4/2001 | Brust et al. | 435/287.2 |
| 6,306,578 | B1 | | 10/2001 | Schellenberger | |
| 6,312,886 | B1 | * | 11/2001 | Lee et al. | 435/4 |
| 6,556,940 | B1 | * | 4/2003 | Tretiakov et al. | 702/130 |
| 6,558,947 | B1 | * | 5/2003 | Lund et al. | 435/303.1 |
| 2002/0001546 | A1 | | 1/2002 | Hunter et al. | |
| 2002/0015994 | A1 | | 2/2002 | Schellenberger et al. | |

FOREIGN PATENT DOCUMENTS

| | | |
|---|---|---|
| WO | WO 99/34920 | 7/1999 |
| WO | WO 01/07890 A2 | 2/2001 |
| WO | WO 01/61054 A2 | 8/2001 |
| WO | WO 01/72424 A1 | 10/2001 |

* cited by examiner

*Primary Examiner*—David A. Redding
(74) *Attorney, Agent, or Firm*—Nydegger & Associates

(57) ABSTRACT

A holding plate for selectively heating and cooling samples in a solution has two opposing surfaces, and a plurality of cylindrically-shaped through-hole wells for holding the samples. Each well extends between the two surfaces of the holding plate, and has an aspect ratio of greater than 5:1, and a diameter less than approximately 500 microns. A metallic coating is applied by vapor deposition techniques on a surface of the holding plate. Importantly, this coating extends into each well through a distance of approximately one and a half well diameters for contact with the solution and the samples. A heat transfer device is thermally connected to the metallic coating for selectively heating and cooling the samples in the wells of the holding plate.

20 Claims, 1 Drawing Sheet

DEVICE FOR EFFECTING HEAT TRANSFER WITH A SOLUTION HELD IN A THROUGH-HOLE WELL OF A HOLDING TRAY

FIELD OF THE INVENTION

The present invention pertains to systems and methods for thermally heating and cooling fluid solutions. More particularly, the present invention pertains to systems and methods for selectively heating and cooling samples held in a plurality of through-hole wells of a holding plate. The present invention is particularly, though not exclusively, useful as a system for selectively heating and cooling samples held in fluid solutions in through-hole wells of a holding plate by establishing effective thermal communication through a metallic coating that extends from the surface of the holding plate into the lumen of each well.

BACKGROUND OF THE INVENTION

Specimen samples may be required to be heated or cooled for various applications. Some applications, however, may require specimen samples to be subjected to thermocycling which involves alternating from high temperatures to lower temperatures for a particular length of time at each temperature. For example, one such application is the amplification of nucleic acid sequences in a process known as polymerase chain reaction (PCR).

Depending on the equipment that is being used, and the particular procedure (application) that is being followed, the heating and cooling of specimen samples will require several considerations. Specifically, one consideration includes the length of time for the change in temperature to occur. This is so because it may be desirable for a temperature change to occur either as rapidly as possible or with very slow, controlled variations. An additional consideration is maintaining a substantially uniform temperature among the samples which are to be heated and cooled. Also, it may be very important for all the samples to experience the same change in temperature at the same time. To further these considerations, it is important to have an efficacious transfer of heat from a heat transfer device to the samples. This is so, regardless of whatever tray, plate or other holding device is being used for holding the samples.

It is well known that holding plates are widely used for holding large numbers of small samples for use in various testing procedures. When temperature control, or predetermined temperature variations are required for the testing or analysis of samples, there must be effective thermal communication between some type of heat transfer device and the samples. For instances wherein the samples are being held in the many through-hole wells of the holding plate, the structure of the holding plate can become important. This situation can become particularly complicated when the material of the holding tray is a poor thermal conductor and access to samples is difficult because the diameters of the through-hole wells in the holding plate are very small.

In light of the above, it is an object of the present invention to provide a system and method for selectively heating and cooling samples in a solution in through-hole wells of a holding plate by establishing an effective thermal communication between the surface of the holding plate and the samples which are to be heated and cooled. Another object of the present invention is to provide a system and method for selectively heating and cooling samples with minimal effect from ambient environmental conditions. Yet another object of the present invention is to provide a system and method for selectively heating and cooling samples which is effectively easy to use, relatively simple to manufacture and comparatively cost effective.

SUMMARY OF THE PREFERRED EMBODIMENTS

A system and method for selectively heating and cooling samples in a solution includes a holding plate having two substantially flat, rectangular-shaped opposing surfaces, and a plurality of through-hole wells for holding the samples and solution. With the wells being formed through the holding plate between the opposing surfaces, each well has a first end and a second end with a preferred aspect ratio of preferably greater than about 5:1. Further, each well of the present invention is generally cylindrical-shaped and it preferably has a diameter of less than approximately five hundred microns.

For the present invention, a metallic coating is positioned, using vapor deposition techniques (e.g. sputtering), on one of the opposing surfaces of the holding plate. Importantly, as a result of the vapor deposition process, this coating will extend into the lumen of each well to contact a solution that is being held in the wells. For the present invention, it is envisioned that the metallic coating will extend a distance of approximately one and one half well diameters (e.g. approximately 750 microns) or as much as two to three diameters into the lumen of each well for contact with the solution in the wells. In an alternate embodiment of the present invention, it is contemplated that the metallic coating can be disposed on both opposing surfaces of the holding plate, and into each well lumen from both ends of the through-hole wells. In either case, since the well diameters are very small, this metallic coating is disposed on the holding plate using any suitable vapor deposition techniques.

For the present invention, a heat transfer device is thermally connected to the metallic coating to establish thermal communication between the heat transfer device and the metallic coating on the surface of the holding plate. Since the metallic coating extends into the well lumens, and is in contact with the solution held in these wells, this coating interconnects the heat transfer device with the solution in the wells. When activated, the heat transfer device will heat or cool the solution and the samples, as desired, via the metallic coating.

In addition to the holding plate, the system of the present invention can include a cap member that is engageable with the holding plate to cover at least one of the opposing surfaces of the plate. As envisioned for the present invention, the cap member will protect the solution and the samples from any ambient environmental conditions, such as evaporation or condensation. Further, by covering the holding plate with the cap member, any spilling or leaking of the solution from the wells can be prevented.

In the operation of the present invention, the wells of the holding plate are first filled with samples in a solution. When the heat transfer device is activated, a thermal communication is established between the device and the solution through the metallic coating on the holding plate. Via the metallic coating, the samples and solution can be heated or cooled, as is necessary for an intended purpose.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
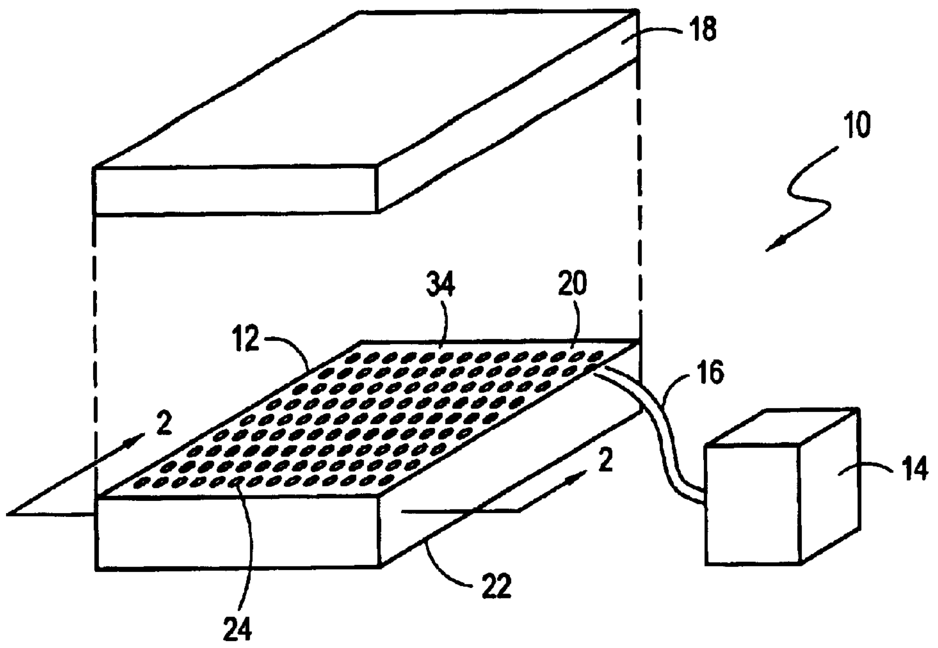
FIG. 1 is an exploded perspective view of the present invention, with a cap member shown positioned above the holding plate for engagement therewith.

Referring initially to FIG. 1, a system for selectively heating and cooling samples in a solution in accordance with the present invention is shown and generally designated 10. As shown, the system 10 includes a holding plate 12 and a heat transfer device 14 that is connected to the holding plate 12 by way of a heat pipe 16, wire or any other means well known in the pertinent art for the purpose of affecting heat transfer. FIG. 1 also shows a cap member 18 that is engageable with the holding plate 12.

Still referring to FIG. 1, in detail, the holding plate 12 is shown to have a first (upper) surface 20 and an opposite second (lower) surface 22. Both of these surfaces 20, 22 are substantially flat and rectangular-shaped. Further, the holding plate 12 is formed with a plurality of through-hole wells 24 that are substantially cylindrical-shaped. These wells 24 are formed between the first and second surfaces 20 and 22 of the holding plate 12 and can be filled with samples in a solution. This filling can be accomplished by any means well known in the art, such as by a wicking action. The structural details of the through-hole wells 24 can perhaps be best seen in FIG. 2.

Figure 2:
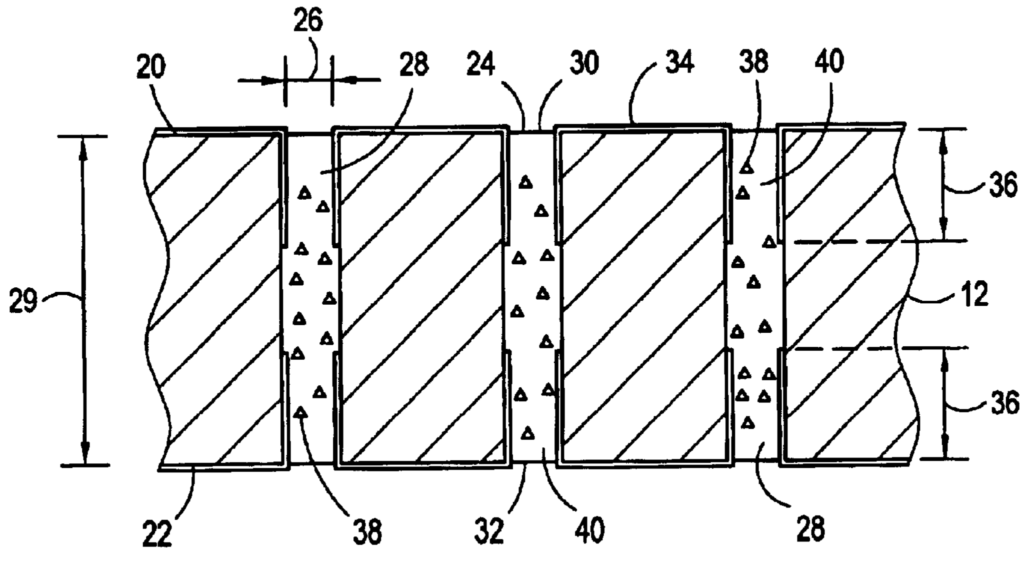
FIG. 2 is a cross-sectional view of the present invention as seen along the lines 2—2 in FIG. 1.

As shown in FIG. 2, each well 24 has a lumen 28 with a length 29 and it has a first end 30 and a second end 32. Also, the lumen 28 has a diameter 26. Specifically, the well diameter 26 of the present invention is approximately less than five hundred microns. Further, each well 24 has a preferred aspect ratio of greater than 5:1. For the through-hole wells 24, this aspect ratio is defined as the ratio of the length 29 of a well 24 to its diameter 26.

Still referring to FIG. 2, the system 10 of the present invention includes a metallic coating 34 that is positioned on the first surface 20 of the holding plate 12. Importantly, as also shown, this metallic coating 34 extends a distance 36 into each lumen 28 to contact the samples 38 in the solution 40 that are held in the wells 24. In order to contact the solution 40, it is contemplated that the metallic coating 34 extends a distance 36 of approximately one and a half well diameters (approximately 750 microns) into each lumen 28. In some applications the distance 36 may be as much as two or three diameters. The metallic coating 34 can be made of any suitable metal well known in the pertinent art, such as Nichrome or Gold. The metallic coating 34 of the present invention is disposed on the holding plate 12 using any suitable vapor deposition techniques.

As contemplated for the present invention, the metallic coating 34 can also be disposed on the second surface 22 of the holding plate 12 as seen in FIG. 2. In this alternate embodiment of the present invention, the metallic coating 34 will also extend a distance 36 of approximately 750 microns into each lumen 28 for contact with the solution 40.

Referring back to FIG. 1, a heat transfer device 14 is shown connected via a heat pipe 16 with the metallic coating 34 on the first surface 20 of the holding plate 12. The heat transfer device 14 would also be connected to the metallic coating 34 on the second surface 22 of the holding plate 12. Importantly, a thermal communication is established between the heat transfer device 14 and the samples 38 in the solution 40 held in the wells 24 by way of the metallic coating 34. Specifically, the transfer of heat will occur from the heat transfer device 14, through the heat pipe 16, to the metallic coating 34 on the first surface 20 of the holding plate 12, and into each well lumen 28. Since the metallic coating 34 is in contact with the solution 40, the solution 40 will be heated or cooled, as desired.

Still referring to FIG. 1, the system 10 of the present invention can include a cap member 18 that is engageable with the holding plate 12 to cover the first surface 20 of the plate 12. The cap member 18, when engaged with the holding plate 12, will protect the solution 40 and samples 38 from any ambient environmental conditions, such as evaporation or condensation. Further, by covering the holding plate 12 with the cap member 18, any spilling or leaking of the solution 40 and samples 38 from the lumens 28 of the wells 24 can be prevented.

In the operation of the present invention, the wells 24 of the holding plate 12 are first filled with samples 38 in a solution 40. When the heat transfer device 14 is activated, a thermal communication is established between the solution 40 in the wells 24 and the heat transfer device 14, through the metallic coating 34. Via the metallic coating 34, the samples 38 and solution 40 can be heated or cooled, as it is necessary for an intended purpose.

While the particular Device for Effecting Heat Transfer with a Solution Held in a Through-Hole Well of a Holding Tray as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for selectively heating and cooling samples held in solution which comprises:

a holding plate having a first surface and a second surface, with a plurality of substantially parallel through-hole wells extending through said holding plate between said first surface and said second surface for holding said samples in solution therein, wherein said through-hole wells are generally cylindrical and have a diameter;

a metallic coating positioned on said first surface and extending a distance into each said through-hole well to contact said solution in said through-hole well; and a heat transfer device thermally connected with said metallic coating for heating and cooling said solution and said sample.

2. A system as recited in claim 1 wherein said distance into each said through-hole well is at least equal to approximately one and one half said diameters.

3. A system as recited in claim 1 further comprising a metallic coating positioned on said second surface and extending approximately said distance into each said through-hole well to contact said solution in said through-hole well.

4. A system as recited in claim 1 further comprising a cap member, said cap member being dimensioned for engagement with said holding plate to cover said first surface thereof and protect said solution from ambient environmental conditions.

5. A system as recited in claim 1 wherein said metallic coating is positioned using vapor deposition techniques.

6. A system as recited in claim 1 wherein each said through-hole well has an aspect ratio greater than 5:1 and said diameter is less than approximately five hundred microns.

7. A system for selectively heating and cooling a sample which comprises:

a holding plate having a first surface and a second surface, and at least one through-hole well for holding said sample therein, wherein said through-hole well has a diameter of approximately five hundred microns, and further wherein said through-hole well has an aspect ratio greater than 5:1;

a thermal conductor positioned on said first surface and extending a distance into said through-hole well to contact said sample in said through-hole well wherein said distance into each said through-hole well is equal to approximately one and one half said diameters; and a heat transfer device thermally connected with said thermal conductor for heating and cooling said sample.

8. A system as recited in claim 7 wherein said holding plate has a plurality of substantially parallel said through-hole wells extending through said holding plate between said first surface and said second surface for holding said sample therein.

9. A system as recited in claim 7 wherein said thermal conductor is a metallic coating.

10. A system as recited in claim 9 wherein said metallic coating is Nichrome.

11. A system as recited in claim 10 further comprising a metallic coating positioned on said second surface and extending approximately said distance into each said through-hole well to contact said sample in said through-hole well.

12. A system as recited in claim 10 wherein said metallic coating is positioned using vapor deposition techniques.

13. A system as recited in claim 7 further comprising a cap member, said cap member being dimensioned for engagement with said holding plate to cover said first surface thereof and protect said solution from ambient environmental conditions.

14. A method for selectively heating and cooling samples held in a solution which comprises the steps of:

placing said samples in a plurality of substantially parallel through-hole wells of a holding plate, said holding plate having a first surface and a second surface, wherein said plurality of through-hole wells extends through said holding plate between said first surface and said second surface for holding said samples in said solution therein, wherein said through-hole wells are generally cylindrical and have a diameter, and further wherein said holding plate has a metallic coating positioned on said first surface and extended a distance of approximately one and a half diameters into each said through-hole well; and activating a heat transfer device, wherein said heat transfer device is thermally connected with said solution and said sample through said metallic coating.

15. A method as recited in claim 14 wherein said holding plate includes a metallic coating positioned on said second surface and extended a distance into each said through-hole well to contact said solution in said through-hole well.

16. A method as recited in claim 15 wherein said distance into each said well is at least equal to approximately one and one half said diameters.

17. A method as recited in claim 14 further comprising the step of covering said holding plate with a cap member to protect said solution from ambient environmental conditions, said cap member being dimensioned for engagement with said holding plate.

18. A method as recited in claim 14 wherein each said through-hole well has an aspect ratio greater than 5:1 and said diameter is less than approximately five hundred microns.

19. A method for manufacturing a heat transfer system to heat and cool a sample which comprises the steps of:

providing a holding plate having a first surface and a second surface, and at least one through-hole well for holding said sample therein, wherein said through-hole well has a diameter of approximately five hundred microns, and further wherein said through-hole well has an aspect ratio greater than 5:1;

coating said first surface of said holding plate with a metallic coating, wherein said metallic coating extends a distance of at least approximately one and a half diameters into said through-hole well;

selectively coating said second surface of said holding plate with said metallic coating, wherein said metallic coating extends a distance of approximately one and a half diameters into said through-hole well; and interconnecting a heat transfer device with said sample in said through-hole well through said metallic coating.

20. A method as recited in claim 19 wherein said coating step is accomplished by vapor deposition techniques.

* * * * *